United States Patent [19]

Nikias et al.

[11] Patent Number: 4,961,428
[45] Date of Patent: Oct. 9, 1990

[54] NON-INVASIVE METHOD AND APPARATUS FOR DESCRIBING THE ELECTRICAL ACTIVITY OF THE SURFACE OF AN INTERIOR ORGAN

[75] Inventors: Chrysostomos L. Nikias, Needham; Dana H. Brooks, Dorchester, both of Mass.; John H. Siegel, Baltimore, Md.; Miklos Fabian, Delta, Pa.

[73] Assignees: Northeastern University, Boston, Mass.; University of Maryland, Baltimore, Md.

[21] Appl. No.: 189,156

[22] Filed: May 2, 1988

[51] Int. Cl.$^5$ .............................................. A61B 5/04
[52] U.S. Cl. ................................ 128/699; 364/413.13; 364/413.19
[58] Field of Search ............... 128/695, 699, 731, 696, 128/710, 712, 639; 364/413.13, 413.19, 413.2, 413.21, 413.22, 413.23, 413.01, 413.15

[56] References Cited

U.S. PATENT DOCUMENTS

| | | | |
|---|---|---|---|
| 3,902,478 | 9/1975 | Konopasek et al. | 128/2.06 F |
| 3,910,260 | 10/1975 | Sarnoff et al. | 128/2.06 R |
| 3,983,867 | 10/1976 | Case | 128/2.06 G |
| 4,004,577 | 1/1977 | Sarnoff | 128/2.06 R |
| 4,067,971 | 1/1978 | Francis et al. | 424/204 |
| 4,098,267 | 7/1978 | Stein et al. | 128/2.06 G |
| 4,106,495 | 8/1978 | Kennedy | 128/2.06 V |
| 4,111,191 | 9/1978 | Shaw | 128/2.05 F |
| 4,121,576 | 10/1978 | Greensite | 128/2.06 V |
| 4,136,690 | 1/1979 | Anderson et al. | 128/2.06 A |
| 4,216,211 | 8/1980 | Francis | 424/204 |
| 4,296,755 | 10/1981 | Judell | 128/705 |
| 4,305,402 | 12/1981 | Katims | 128/741 |
| 4,367,751 | 1/1983 | Link et al. | 128/682 |
| 4,370,983 | 2/1983 | Lichtenstein | 128/630 |
| 4,416,288 | 11/1983 | Freeman | 128/731 |
| 4,422,459 | 12/1983 | Simson | 128/702 |
| 4,428,381 | 1/1984 | Hepp | 128/715 |
| 4,433,380 | 2/1984 | Abele et al. | 364/413.22 |
| 4,458,691 | 7/1984 | Netravali | 128/705 |
| 4,458,692 | 7/1984 | Simson | 128/705 |
| 4,458,693 | 7/1984 | Badzinski et al. | 128/715 |
| 4,464,172 | 8/1984 | Lichtenstein | 604/65 |
| 4,492,235 | 1/1985 | Sitrick | 12/705 |
| 4,501,279 | 2/1985 | Seo | 128/663 |

(List continued on next page.)

OTHER PUBLICATIONS

Brooks, D. H.; Nikias, C. L.; Siegel, J. H.; A Frequency Domain Inverse Solution in Electrocardiography, Northeastern University Dept. of Electrical and Computer Engin. Commun. & Digital Signal Processing Ctr. Whitaker Found. Grant No. 65745-9044.

Nikias, C. L.; Siegel, J. H., Raghuveer, M. R.; Fabian, M., Spectrum Estimation for the Analysis of Array ECG; Seventh Annual Conference of the Engineering in Medicine and Biology Society, Sep. 27–30, 1985.

Brooks, D. H., Nikias, C. L.; Comparison and Testing of Least–Squares Time Domain Inverse Solutions in Electrocardiography; Northeastern Univ., Dept. of Electrical & Computer Engin., Whitaker Foundation Grant No. 05745-9044.

Primary Examiner—Lee S. Cohen
Assistant Examiner—S. Getzow
Attorney, Agent, or Firm—Weingarten, Schurgin, Gagnebin & Hayes

[57] ABSTRACT

A method and apparatus for processing a plurality of signals provided by an array of electrodes disposed on the surface of the body further comprising a reconstruction of the electrical activity on the surface of a selected interior organ according to the plurality of array signals and a selected model of the body in the region of the interior organ and the electrode array. The reconstruction includes assumptions made according to a priori knowledge of the selected model and permits reconstruction of the electrical activity on the surface of the interior organ and can further provide practical solutions with underdetermined sets of equations. The present inventions further includes reconstruction including a power spectrum analysis of the array signals to permit detection and localizing of a predetermined physiological condition. The power spectrum analysis may further include a frequency domain analysis according to the minimum relative entropy of the measured signals.

10 Claims, 3 Drawing Sheets

U.S. PATENT DOCUMENTS

| | | | |
|---|---|---|---|
| 4,503,863 | 3/1985 | Katims | 128/741 |
| 4,519,395 | 5/1985 | Hrushesky | 128/671 |
| 4,531,527 | 7/1985 | Reinhold, Jr. et al. | 128/696 |
| 4,537,200 | 8/1985 | Widrow | 128/696 |
| 4,539,640 | 9/1985 | Fry et al. | 128/734 |
| 4,569,357 | 2/1986 | Sanz et al. | 128/699 |
| 4,579,125 | 4/1986 | Strobl et al. | 128/731 |
| 4,589,420 | 5/1986 | Adams et al. | 128/702 |
| 4,610,259 | 9/1986 | Cohen et al. | 128/731 |
| 4,630,204 | 12/1986 | Mortara | 364/417 |
| 4,633,881 | 1/1987 | Moore et al. | 128/659 |
| 4,635,296 | 1/1987 | Dinsmore | 455/113 |
| 4,679,144 | 7/1987 | Cox et al. | 364/417 |
| 4,680,708 | 7/1987 | Ambos et al. | 364/417 |
| 4,682,603 | 7/1987 | Franz | 128/642 |
| 4,697,597 | 10/1987 | Sanz et al. | 128/699 |

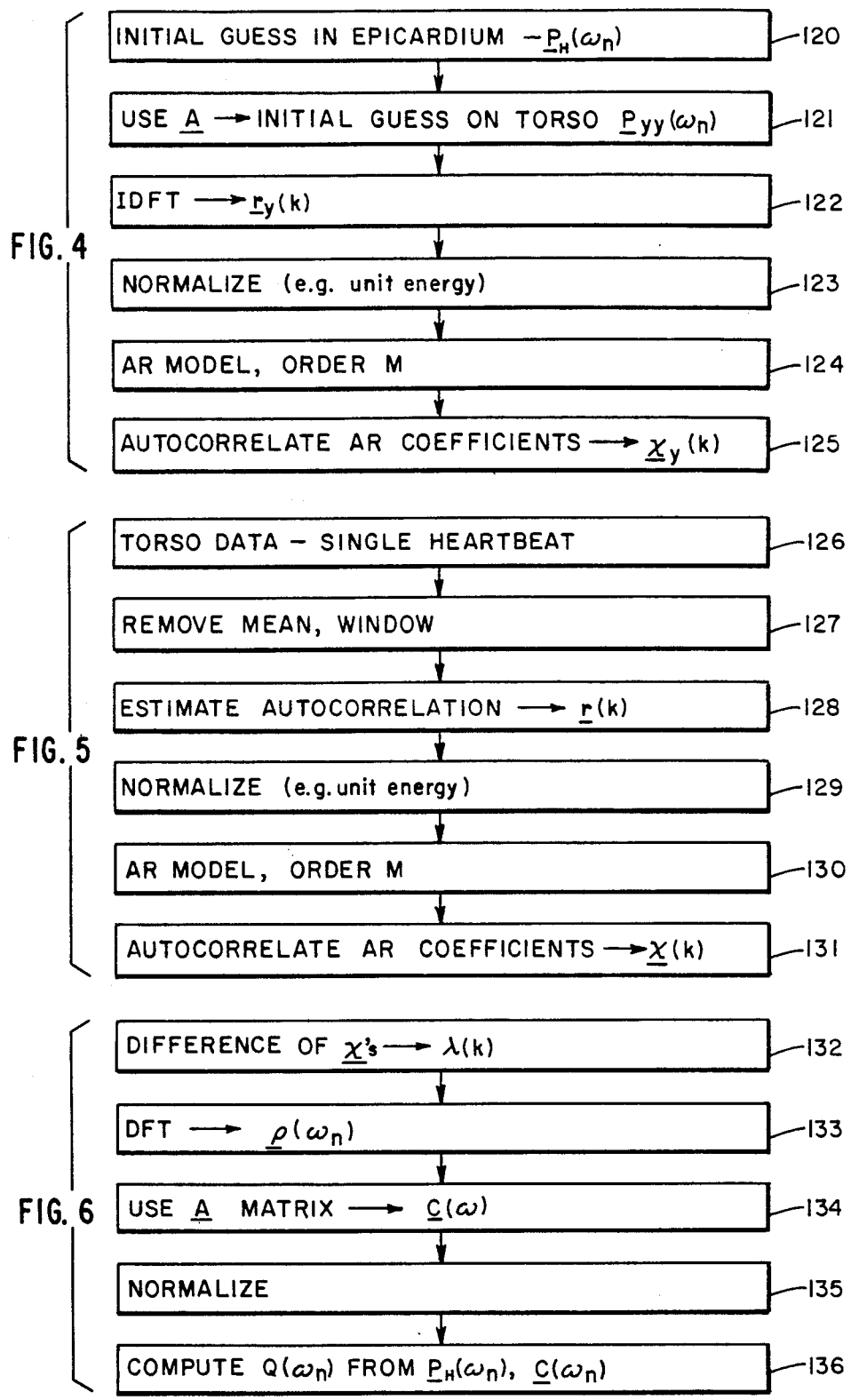

NON-INVASIVE METHOD AND APPARATUS FOR DESCRIBING THE ELECTRICAL ACTIVITY OF THE SURFACE OF AN INTERIOR ORGAN

FIELD OF THE INVENTION

The present invention relates to electrophysiological methods and apparatus for determining the interior electrical activity on the surface of an internal organ and, in particular, such methods and apparatus as applied to frequency domain inverse solutions in electrocardiography.

BACKGROUND OF THE INVENTION

Non-invasive methodologies for assessing the state of health of the heart, such as using a torso array of electrocardiographic (ECG) signals to localize cardiac activity has been of continuing interest. Present methods which approach this problem involve the processing of the ECG torso signals to provide a mapping of cardiac potentials from a particular weighting and processing of the signals, frequently referred to as finding a solution for the inverse problem.

Considered separately from the inverse problem is the forward problem, wherein a model is developed to predict the interaction of the signals produced on the surface of the heart through the section of the human torso to the surface thereof. Such forward solutions as derived from a geometric model of the human torso, prepared according to cross sections of a representative subject derived from imaging techniques such as CAT systems. However, the difficulty involved in representing complex anatomical structures in a mathematically useful form has led many investigators to include simplifying assumptions and including empirical results based on animal experiments. However, limitations in the resulting model, which may differ substantially from the actual subjects anatomy, will adversely affect the solution of the inverse problem. However, the field of electrophysiology, including electrocardiography, historically views the forward and inverse problems, and their solutions, as separate fields of endeavor having different investigators. Therefore, the models developed to solve the forward problem in electrocardiography include unresolved limitations. Furthermore, such models and inherent limitations are frequently not considered in the inverse solution.

Popular realizations of inverse solutions have been based on applications of least squares reconstruction principles as constrained (regularized) least squares (CLS) and singular value decomposition (SVD), which operate in the time-space domain of data. Although these methods offer the advantages of relative algorithm simplicity and the ability to reconstruct signal amplitude as well as shape, they are fairly sensitive to measurement noise and require a large number of body surface sensors to provide accurate results. Furthermore, they require a priori knowledge or an estimate of a parameter whose value can significantly distort the results. Such disadvantages create serious difficulties to successfully implement these methods of inverse solution in a clinical setting.

The above-mentioned limitations of popular methods of electrocardiography further limit their usefulness and accuracy in the detection localization and quantification of cardiac dysfunction, such as myocardial ischemia.

SUMMARY OF THE INVENTION

The methods and apparatus according to the present invention provide clinically useful inverse solutions and electrocardiography to permit successful non-invasive detection, localization and quantification of cardiac defects such as myocardial ischemia, by providing a frequency domain analysis of the parameters in the inverse solution to provide a desired reconstruction of the potentials at the cardiac surface from a smaller number of measured ECG signals. Furthermore, the method and apparatus according to the present invention permits practical solutions for underdetermined and overdetermined data samples, according to an inverse solution determined with particular reference to the model developed in solution to the forward problem in electrocardiography.

The particular implementation discussed below provides an inverse solution based on a minimum relative entropy (MRE) and other reconstruction principles. This method reconstructs the power spectrum of each of the epicardial signals, starting with an initial estimate of each spectrum according to the forward solution, and then applying the MRE principle to constrain the estimate to fit the observed torso data. Significant improvement is made according to the present invention when compared to results obtained with typical least-squares method, i.e., CLS, and permits the use of a smaller array of sensors on the torso surface and exhibit a reduced sensitivity to measured signal noise or other induced error components.

BRIEF DESCRIPTION OF THE DRAWING

These and further features of the present invention will be better understood by reading the following detailed description, taken together with the drawing, wherein:

FIG. 4 is a flow chart showing the computation of estimate-based vectors according to one embodiment of the present invention;

FIG. 5 is a flow chart showing the computation of torso data-based vectors according to one embodiment of the present invention; and FIG. 6 is a flow chart showing the computation of MRE inverse spectral estimates according to one embodiment of the present invention.

DETAILED DESCRIPTION OF THE INVENTION

Figure 1:
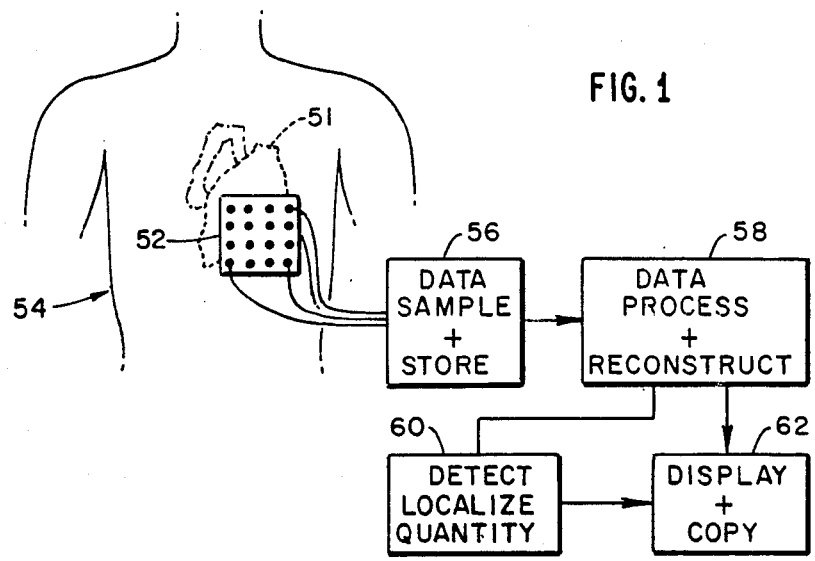
FIG. 1 is a block diagram of the present invention showing connection to the subject for data sampling and storage.

A block diagram 50 of one embodiment of this present invention is shown in FIG. 1. An array of electrodes 52, typically disposed in a rectangular array of m electrodes, e.g., 6x8 array, is disposed on the surface of the torso 54 nearest the organ of interest. Shown in FIG. 1 is the preferred placement to receive electrophysiological signals. The electrode signals are received by a data sample and storage element 56 which provides the electrode signal data as necessary to be processed by the data processor 58, which includes the forward model therein, to provide the desired reconstruction of the signal on the surface of the heart, 51. Further, according to the present invention, a specific physiological condition can be recognized, localized and quantified by element 60, and displayed on element 62 to provide a representative image and hard copy thereof. The recognition and localization of a selected physiological condition is made pursuant to prestored selected reference data and threshold signal values made available to element 60. The elements 56, 58, 60 and 62 are implemented with available physiological sampling, processing and display systems including systems having miniaturized signal processing elements.

Figure 2A:
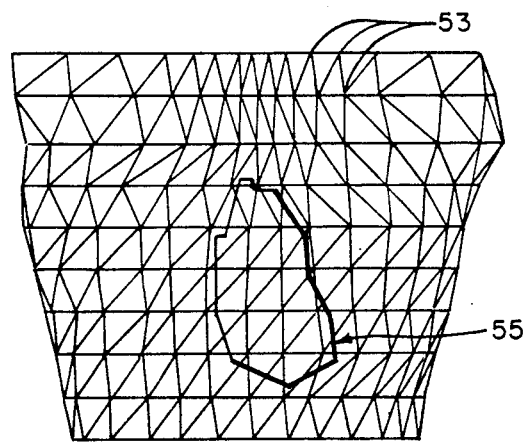
FIGS. 2A–2C are front reconstructions of the heart, lungs and spine of a subject.
Figure 2D:
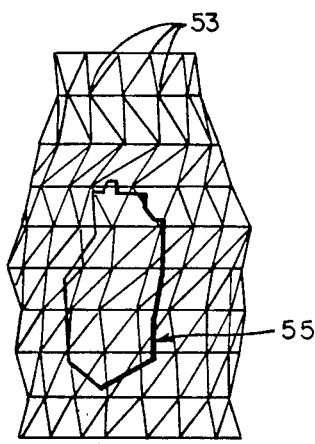
FIGS. 2D–2F are lateral reconstructions of the heart, lungs and spine of the subject according to the reconstruction method of one embodiment of the present invention.
Figure 2B:
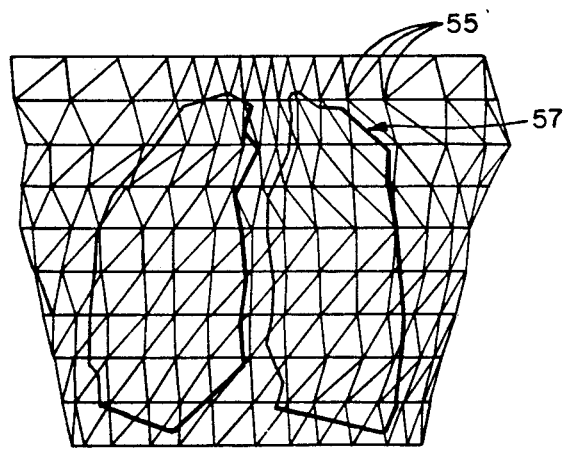
Figure 2E:
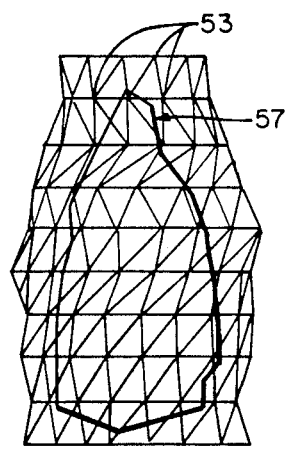
Figure 2C:
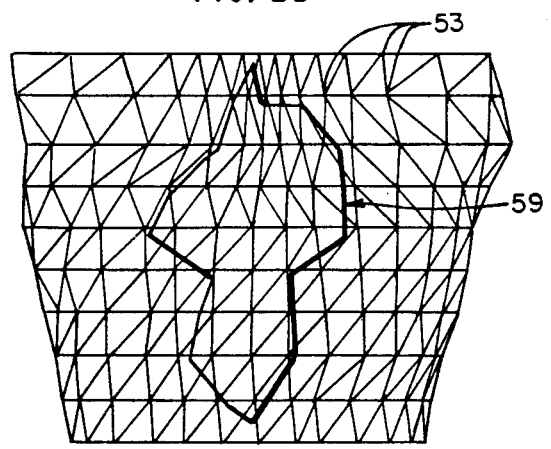
Figure 2F:
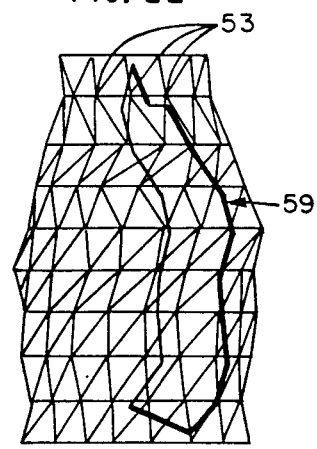

Representative resulting images produced according to the system of FIG. 1 are shown in FIGS. 2A-2F, wherein elevated frontal views are shown in FIGS. 2A-2C and elevated side views are shown in FIGS. 2D-2F. A reconstruction of the surface of the torso is provided from point 53 and the reconstruction of the surface of the heart, lungs and spinal column is shown from points 55, 57 and 59, respectively.

The forward model can be represented by the equation $$v(k) = Ah(k) \tag{1}$$

where $v(k) = [v_1(k), v_2(k), \ldots, v_M(k)]^T$ is the Mx1 vector of the M torso potentials at time k, k=1, 2, ..., L (=32); where $h(k) = [h_1(k), h_2(k), \ldots, h_N(k)]^T$ is the Nx1 vector of epicardial potentials at time k; and where and A is the MxN transfer matrix whose coefficients represent the forward effect of the torso volume conductor. The forward model is implemented by computing the coefficients of the matrix A. The inverse methods were then applied to subsets of the torso data from m sensors ($0 < m \leq M$), $v_m(k)$, using the mxN submatrix $A_m$ containing m rows of A which correspond to the m sensors in the chosen torso array, and applied to solve the inverse problem of a subset of equation (1) and compute h(k). However A is not only not constrained to be square but is also inherently ill-conditioned.

For purposes of simplicity, in the ensuing discussion the particular torso submatrix $A_m$ is referred to simply as a and consider it to be an MxN matrix and the torso data vector $v_m(k)$ simply as v(k).

Using the human anatomy of FIG. 1 and assuming that a realistic forward model is described by equation (1), $$\begin{aligned} v_i(k) &= a_i^T h(k); \\ k &= 1, 2, \ldots, L \\ i &= 1, 2, \ldots, M \end{aligned} \tag{2}$$

where $v_i(k) = i^{th}$-sensor body surface potential at time instant (k), $h(k) = [h_1(k), h_2(k), \ldots, h_N(k)]^T$ (N×1) are the epicardial potentials, and $a_i^T = [a_{i1}, \ldots, a_{iN}]$ (N×1) is the $i^{th}$-row of the forward coefficient matrix then the autocorrelation sequence, $R_i(m)$, of the $i^{th}$-sensor body surface potential is related to the multichannel correlation matrix of the epicardial potentials, $R_h(m)$, as follows:

$$R_i(m) = a_i^T R_h(m) \, a_i \tag{3}$$

$$1 \times 1 \quad 1 \times NN \quad NN \times NN \quad NN \times 1$$

where $R_i(m) = \frac{1}{L} \sum_k v_i(k) \, v_i(k+m)$ and $R_h(m) = \frac{1}{L} \sum_k h(k) \, h^T(k+m)$.

Since $R_h(m) = \sum_n H(\omega_n) \, e^{j\omega_n m}$.

where $H(\omega)$ is (N×N) multichannel spectrum matrix of epicardial potentials, it follows from equation (3) that $$R_i(m) = \sum_n a_i^T H(\omega_n) \, a_i \, e^{j\omega_n n}. \tag{4}$$

Assuming that the Fourier coefficients of h(k), $x_n$, are Gaussian random variables, i.e., $$f(x_n) \simeq N(0, H(\omega_n))$$

and uncorrelated, then their joint multivariate probability density function (PDF) is given by $$f(x) = f(x_1).f(x_2) \ldots f(x_R).$$

Repeating the same assumptions for an initial estimate multichannel spectral matrix $P(\omega_n)$ (NxN) we have $$p(x_n) \simeq N(0, P(\omega_n))$$

and $$p(x) = p(x_1).p(x_2) \ldots p(x_R).$$

Adopting the Minimum Relative Entropy (MRE) reconstruction principle (Kullback Information Measure), for one embodiment of the present invention, we have the following formulation:

$$\text{Minimize } H_1 = -\int f(x) \log [f(x)/p(x)] dx \tag{5}$$

subject to the constraints $$\begin{aligned} \sum_n a_i^T H(\omega_n) \, a_i \, e^{j\omega_n m} &= R_i(m) \\ i &= 1, 2, \ldots, M \\ m &= 0, 1, \ldots, J \\ H(\omega_n) &\geq 0 \\ n &= 1, 2, \ldots, R \end{aligned}$$

This is a nonlinear problem that is solved, in general, by a nonlinear gradient search technique. However, the nonlinearity can be bypassed if the torso and epicardial potentials are modeled as autoregressive processes.

Other embodiments of the present invention provide the following integral equations (5A-5C) which may be substituted for (5) and solved subject to the same constraints:

(1) Minimum Energy $$\text{Minimize } E = \int f^2(x) \, dx \tag{5A}$$

or (2) Maximum Entropy (Boltzman)

$$\text{Maximize } H_2 = \int f(x) \log f(x) \, dx \tag{5B}$$

or (3) Maximum Entropy (Shannon)

$$\text{Maximize } H_3 = \int \log f(x) \, dx \quad (5C)$$

A specific implementation is now discussed. Data on the geometry of the epicardium, torso surface, and electrically significant internal organs are obtained from CT-scan sections or other sources in the flow chart of FIG. 3. Data may come from measurements made on the individual patient (e.g., digitized CT-scan sections), from a data base for patients with similar anatomies, from another appropriate source, or from a combination of these sources (e.g., measured data for the individual's epicardium combined with data base information for the other organs). Estimates of the electrical conductivity of the various internal organs, relative to the conductivity of the surrounding medium, are also obtained from individual measurements or previously reported or acquired data. The acquisition of this geometric and conductivity data is represented by block 110. In block 111 we calculate the "forward coefficients" or "constraint equations" of the forward model, which represent the forward effect of the torso volume conductor on the ECG signals propagating outward from the epicardium. These coefficients use the geometric and conductivity data from block 110 as input to either of the standard methods reported in the literature, the "solid angle method" or the "finite element method," to a modification of either of these methods, for instance by incorporating organ conductivity estimated probability densities into the procedure, or to any new method which proves desirable. In block 112 we show the assumption of initial estimate matrices of multichannel auto and cross power spectra of the epicardial signals at each location represented in the geometric model of block 110. This initial estimate may be a white "flat" spectrum, it may be based on a standard "least squares" inverse solution such as constrained least squares or singular value decomposition, or it may be based on any appropriate and available a priori information. In addition it may be uncorrelated (i.e., all cross spectra identical to zero) but a general correlated case is also possible. This initial estimate is projected forward onto the torso sensor locations using the forward coefficient matrix and then normalized by a convenient and consistent method such as a unit energy per signal constraint. The resulting "initial estimate" matrices give auto and cross spectra at each location on the torso at which data is to be taken. Autocorrelations are obtained using Inverse Discrete Fourier Transform (IDFT) operations and then used to obtain an autoregressive (AR) model in block 113. The order of the AR model can be chosen a priori from previous experience or determined through model order selection criteria on estimated torso data autocorrelations. The AR coefficients are then autocorrelated to give the "initial estimate" vectors $\psi_y(k)$. Blocks 110 and 113 are performed before the MRE inverse analysis is applied to the actual torso array data. If the initial estimate and the model order do not depend on the torso data (e.g., if a white initial estimate is used) then blocks 110 to 113 may be performed off-line, as soon as the geometric and conductivity data are obtained.

Array ECG data is recorded, filtered, sampled, and pre-processed to produce blocks of array data, each from a single heartbeat, as shown in block 114. A multichannel AR model of the same order as that used in block 113 is fitted to the normalized estimated autocorrelations of the data in block 115 and the AR coefficients are autocorrelated to calculate the "data based" vectors $\psi(k)$.

The "correction" vectors $\lambda(k)$ are calculated in block 116 as the difference between the "data based" and "initial estimate based" vectors $\psi(k)$ and $\psi_y(k)$, i.e., $\lambda(k) = \psi(k) - \psi_y(k)$. A DFT of these "correction vectors" is taken (block 117) to transform them from the autocorrelation domain to the spectrum domain and then the forward coefficient matrix is used in block 118 to project these matrices back onto the epicardial surface locations. Proper normalization is used to reconcile the resulting correction matrices energy assumptions with those of the initial estimate epicardial spectral matrices. The initial estimate matrices are then improved in block 119 by combining them with the correction matrices according to the MRE equations to produce the MRE estimate of the multichannel auto and cross power spectra at each epicardial location.

FIG. 4 is a flow chart for a computer program to compute the initial estimate based vectors $\psi_y(k)$, a function performed in FIG. 1 by blocks 112 and 113. An initial estimate of the epicardial spectra, $P_H(\omega_n)$, where $\omega_n$ are discrete frequencies, is assumed or calculated in block 20 as described above for block 112. Using the forward transfer matrix A from block 111 in block 121, the initial estimate torso power spectra $P_{yy}(\omega_n)$ are computed from $P_H(\omega_n)$. An IDFT is performed in block 122 to obtain the initial estimate based torso autocorrelations $r_y(k)$. In block 123 we normalize these autocorrelations to enable consistency with the data-based autocorrelations, for example, by forcing each signal to have unit energy. In block 124 we calculate an AR model of predetermined order M of the torso initial estimate, using, for example, the well-known Levinson recursion algorithm. Autocorrelating the resultant AR coefficients produces the initial estimate based vectors $\psi_y(k)$, as shown in block 125.

Figure 3:
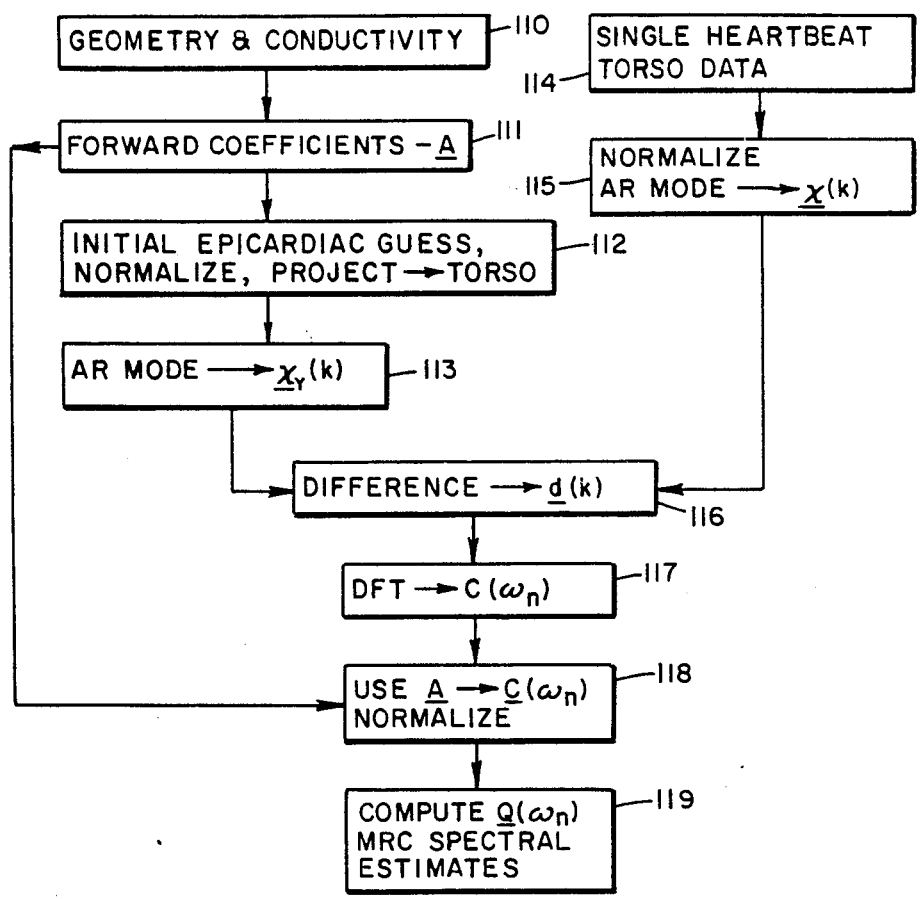
FIG. 3 is a flow chart of the forward and inverse modelling process according to one embodiment of the present invention.

FIG. 5 is a flow chart for a computer program to compute the torso data based vectors $\psi(k)$, a function performed in FIG. 3 by blocks 114 and 115. In block 126 we obtain torso data for a single heartbeat from each sensor in our torso sensor array as described above for block 114. In block 127 we remove the sample mean of the data and apply a smoothing window function such as the Hamming window. Biased autocorrelation estimates are calculated in block 128. Normalization by a constraint consistent with the initial estimate (such as unit energy) is applied in block 129. An AR model of order M (as in block 124) is then fitted to the torso data, block 130. The autocorrelations of the resulting AR coefficients are calculated in block 131, producing the data based vectors $\psi(k)$.

FIG. 6 is a flow chart for a computer program to compute the MRE inverse spectral estimates, a function performed in FIG. 3 by blocks 116 to 119. In block 132 we calculate the $\psi(k)$ vectors as the difference between the data based vectors $\psi(k)$ and the initial-estimate based vectors $\psi_y(k)$. For the special case where the initial estimate is both white and uncorrelated (i.e., $P_H(\omega_n)$ is equal for all $\omega_n$ and diagonal) and where unit energy normalization is employed in block 129, $\lambda(k)$ will be the same as $\psi(k)$ for $k \neq 0$ and will equal $\psi(k) - 1$ for $k = 0$, and the program shown in FIG. 4 can be bypassed. A DFT is performed on $\lambda(k)$, resulting in a signal $\rho(\omega_n)$, as shown in block 133. Using the forward model matrix A, we project this torso spectral difference signal $\rho(\omega_n)$ onto the epicardial locations in block 134. We normalize again to account for the scaling effect of the coefficients of A, producing the epicardial spectral correction matrices $C(\omega_n)$ in block 135. In block 136 we implement the MRE equation and calculate the MRE auto and cross spectral estimates from the correction matrices $C(\omega_n)$ and the epicardial initial estimate spectral matrices $P_H(\omega_n)$, i.e., $$O(w_n) = [P(w_n)^{-1} + P_H(w_n)C(w_n)]^{-1} \qquad (6)$$

Modifications and substitutions made by one of ordinary skill in the art, such as alternative, nonrectangular array configurations, computational and display systems, are within the scope of the present invention, which is not limited except by the scope of the following claims.

What is claimed is:

1. A method of reconstructing the electrical activity on the surface of an interior organ according to a plurality of non-invasively measured epidermal signals, comprising the steps of:
   preparing a selected forward model;
   adjusting the forward model according to selected physiological criteria;
   recording said plurality of epidermal signals from an electrical array;
   reconstructing a power signal spectrum of the electrical signals of a selected interior surface according to
   said selected forward model, and
   said recorded epidermal signals.

2. The method of claim 1, wherein
   said power signal spectrum comprises a frequency domain analysis according to the minimum relative entropy (MRE).

3. The method of claim 2, wherein relative Entropy is minimized according to Minimize $H_1 = \int f(x) \log [f(x)/p(x)] dx$.

4. The method of claim 3, wherein
   a computationally efficient situation is obtained by the approximation of epidermal signals as autoregressive processes wherein
   the non-linearity of the minimum relative entropy solution is avoided.

5. The method of claim 1, wherein said power spectrum estimation minimizes Energy according to Minimize $E = \int f^2(x) dx$.

6. The method of claim 1, wherein said power spectrum estimation maximizes Entropy according to Maximize $H_2 = \int f(x) \log f(x) dx$.

7. The method of claim 1, wherein said power spectrum estimation maximizes Entropy according to Maximize $H_3 = \int \log f(x) dx$.

8. The method of claim 1 further including the step of localizing a physiological condition determined according to a comparison of the reconstructed power spectrum of each signal to selected threshold criteria.

9. Apparatus for reconstructing the electrical signals on the surface of a selected interior organ according to a plurality of non-invasively measured epidermal signals, comprising:
   means for preparing a selected forward model, said forward model being adjusted by selected physiological criteria;
   means for recording said non-invasively measured epidermal signals;
   means for providing a power spectrum estimate of said epidermal signals;
   signal processing means for reconstructing a power signal spectrum of the electrical signals on the surface of said selected organ according to said power spectrum estimate and said recorded epidermal signals and the adjusted forward model.

10. The apparatus of claim 9, wherein,
    said means for providing a power spectrum estimate includes processing means for providing said power spectrum estimate according to one of:

Minimize $H_1 = \int f(x) \log [f(x)/p(x)] dx$;

Minimize $E = \int f^2(x) dx$;

Maximize $H_2 = \int f(x) \log f(x) dx$; and

Maximize $H_3 = \int \log f(x) dx$.

* * * * *

UNITED STATES PATENT AND TRADEMARK OFFICE
CERTIFICATE OF CORRECTION

PATENT NO. : 4,961,428

DATED : October 9, 1990

INVENTOR(S) : Chrysostomos L. Nikias, et al.

It is certified that error appears in the above-identified patent and that said Letters Patent is hereby corrected as shown below:

Column 3, line 34, "where and A is" should read --where A is--.

Column 4, line 51, "n) $\geq$ 0" should read --n) $\geq$ 0--.

Signed and Sealed this

Twenty-seventh Day of October, 1992

Attest:

DOUGLAS B. COMER

Attesting Officer   Acting Commissioner of Patents and Trademarks